4,612,302

United States Patent [19]

Szabo et al.

[11] Patent Number: 4,612,302

[45] Date of Patent: Sep. 16, 1986

[54] CLINICAL USE OF SOMATOSTATIN ANALOGUES

[75] Inventors: Sandor Szabo, Brookline, Mass.; Klaus W. Usadel, Weinheim; Horst Kessler, Schwalbach, both of Fed. Rep. of Germany

[73] Assignee: Brigham and Women's Hospital, Mass.

[21] Appl. No.: 550,978

[22] Filed: Nov. 14, 1983

[51] Int. Cl.[4] .......................... A61K 37/24; C07K 7/26
[52] U.S. Cl. ........................................ 514/11; 514/806; 530/311
[58] Field of Search ................. 260/112.5 S; 514/806, 514/11

[56] References Cited

U.S. PATENT DOCUMENTS

| | | | |
|---|---|---|---|
| 4,224,199 | 9/1980 | Meyers et al. | 260/112.5 S |
| 4,280,953 | 7/1981 | Guillemin et al. | 260/112.5 S |
| 4,310,518 | 1/1982 | Freidinger et al. | 260/112.5 S |
| 4,316,890 | 2/1982 | Kamber et al. | 260/112.5 S |
| 4,316,891 | 2/1982 | Guillemin et al. | 260/112.5 S |
| 4,328,214 | 4/1982 | Rink et al. | 260/112.5 S |
| 4,360,516 | 11/1982 | Freidinger et al. | 260/112.5 S |
| 4,366,148 | 12/1982 | Szabo et al. | 260/112.5 S |
| 4,369,179 | 1/1983 | Rink et al. | 260/112.5 S |

OTHER PUBLICATIONS

Veber et al., *Nature*, 292, 55–58, (1981).

*Primary Examiner*—Delbert R. Phillips
*Attorney, Agent, or Firm*—Oblon, Fisher, Spivak, McClelland & Maier

[57] ABSTRACT

A method of increasing the clearance of particles from the blood stream of a vertebrate, which comprises administering to a vertebrate having a surplus of particles in the blood stream of the vertebrate an amount of a somatostatin analogue sufficient to increase phagocytosis in the vertebrate is disclosed along with a method treating vascular lesions or deterioration of biological membranes comprising the step of administering to a human or other mammal suspected of having one or more vascular lesions or of having deterioration of a biological membrane in the liver of said human or mammal an amount of a somatostatin analogue sufficient to reduce the number or severity of said lesions or to prevent further deterioration or reduce the extent of deterioration of said membrane.

21 Claims, No Drawings

CLINICAL USE OF SOMATOSTATIN ANALOGUES

BACKGROUND OF THE INVENTION

1. Field of the Invention

This invention relates to analogues of the cyclic peptide hormone somatostatin and to methods of stimulating phagocytosis and of protecting tissues from toxins.

2. Description of the Prior Art

Somatostatin is a peptide hormone originally investigated because of its inhibitory effects against pituitary growth hormone, which is also known as somatotropin. Somatostatin is therefore sometimes known as somatotropin release inhibiting factor (SRIF). Recent studies have shown that pretreatment with exogenous somatostatin prevents cysteamine-induced duodenal ulcer, with minimal inhibition of gastric acid output (Schwedes et al, *Eur. J. Pharm.*, 44, 195 (1977)). In addition, somatostatin has been shown to have a beneficial effect on experimentally induced pancreatitis (Schwedes et al, *Horm. Metab. Res.*, 11, 142 (1979)) and adrenal and lung lesions (Schwedes et al, *Metabolism Suppl.*, 1, 27, 1377 (1978)). Thus, somatostatin has been demonstrated to be useful in the protection of various tissues against damage, as well as for its original/property as a pituitary growth hormone inhibitor.

Additionally, various derivatives and analogues of somatostatin have been prepared for a variety of other purposes. The following U.S. patents are exemplary of these disclosures.

U.S. Pat. No. 4,310,518 discloses compounds of the formula $$\begin{array}{c}
R_5 \quad O \quad R_2 \quad O \quad R_3 \quad O \\
| \quad \| \quad | \quad \| \quad | \quad \| \\
CH-C-NH-CH-C-NH-CH-C \\
| \qquad\qquad\qquad\qquad\qquad | \\
CH_3-N \qquad\qquad\qquad\qquad NH \\
| \qquad\qquad\qquad\qquad\qquad | \\
C-CH-NH-C-CH-NH-C-CH-CH_2YCH_2CH_2NH_2 \\
\| \quad | \qquad\quad \| \quad | \qquad\quad \| \\
O \quad R_1 \qquad O \quad R_4 \qquad O
\end{array}$$

wherein

Y is $(CH_2)_m$ wherein m is 0, 1 or 2 or sulfur such that the sulfur may be in any position along the chain;

$R_1$ and $R_2$ are independently lower alkyl, benzyl, substituted benzyl where the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lower alkoxy, hydroxy, halogen amino or nitro. These compounds are disclosed as having a more selective biological activity than somatostatin and to useful as growth hormone inhibitors and in the treatment of acromegaly, diabetes, diabetic retinopathy and peptic ulcers.

U.S. Pat. No. 4,360,516 discloses compounds of the formula $$\begin{array}{c}
R_5 \qquad O \quad R_2 \qquad O \quad R_3 \\
| \qquad\quad \| \quad | \qquad\quad \| \quad | \\
CH-NH-C-CH-NH-C-C^*H \\
| \qquad\qquad\qquad\qquad\qquad\qquad | \\
O=C \qquad\qquad\qquad\qquad\qquad\quad NH \\
| \qquad\qquad\qquad\qquad\qquad\qquad | \\
CH_3-N \qquad\qquad\qquad\qquad\qquad C=O \\
| \qquad\qquad\qquad\qquad\qquad\qquad | \\
CH-C-NH-CH-C-NH-C^*HCH_2YCH_2CH_2NH_2 \\
| \quad \| \qquad\quad | \quad \| \\
R_1 \quad O \qquad\quad R_4 \quad O
\end{array}$$

wherein

Y is $(CH_2)_m$ wherein m is 0, 1, or 2 or sulfur such that the sulfur may be in any positiion along the chain;

$R_1$ and $R_2$ are independently lower alkyl, benzyl, substituted benzyl where the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lower alkoxy, hydroxy, halogen amino or nitro; and the two asymmetric centers marked with an asterisk (*) may be either D or L, provided the two centers of asymmetry are the same, while the other asymmetric centers are D. These compounds inhibit the release of glucagon, growth hormone and insulin, and certain of the compounds are also capable of inhibiting the release of gastric acid secretions. The compounds are said to be particularly useful in the treatment of acromegaly, diabetes, diabetic retinopathy and peptic ulcers.

U.S. Pat. No. 4,224,199 discloses compounds of the formula

H—Ala—Gly—Cys—Lys—Asn—Phe—Phe—A—
—Lys—Thr—Phe—Thr—Ser—Cys—OH in which A represents an L-, D- or DL-5- or 6-fluoro-, bromo-, chloro-, or iodotryptophyl radical. These tetradecapeptides inhibit the release of growth hormone.

U.S. Pat. No. 4,316,890 discloses compounds of the formula

Bmp—Lys—X—Phe—trp—Lys—Thr—Phe—Thr—Y—Cys—OH in which

Bmp represents a desaminocysteine radical,

X represents Asn or His, trp represents D-Trp that may be substituted in the phenyl ring by a halogen atom, and Y represents the radical of a secondary α-amino acid having a maximum of 8 carbon atoms. These compounds have strong insulin-antagonistic and glucagon-antagonistic effects and are useful as antidiabetics.

U.S. Pat. No. 4,369,179 discloses compounds of the formula

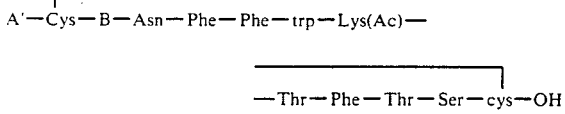

in which

A' represents H-Ala-Gly-, Ac-Ala-Gly-, H- or Ac-.

B represents Lys, Lys(Ac) or Lys(X) (wherein X is an ε-amino-protecting group)

trp represents L-Trp, D-Trp or an analogous radical which carries in the indole nucleus a halogen atom, cys represents L-Cys or D-Cys and Ac represents an acyl radical of an optionally substituted alkanecarboxyclic acid present at the free amino group. These compounds can be used as antidiabetics or to combat gastrointestinal bleeding.

U.S. Pat. No. 4,328,214 discloses compounds of the formula

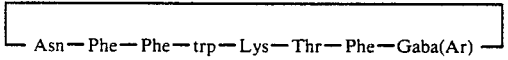

in which trp represents L-Trp or D-Trp in which the phenyl ring may be substituted with a halogen atom, and Gaba(Ar) represents the residue of a γ-aminobutyric acid substituted with a cyclic hydrocarbyl radical. These compounds are disclosed to be antidiabetics.

U.S. Pat. No. 4,316,891 discloses compounds of the formula

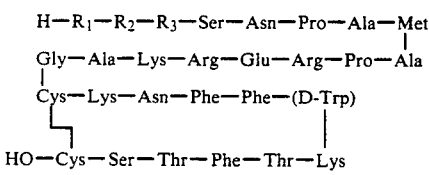

in which $R_1$ is Ser or des $R_1$, $R_2$ is Ala or des $R_2$, and $R_3$ is Asn or des $R_3$ and linear versions thereof in which the disulfide bridge is replaced by hydrogen sulfides. These compounds are more potent than somatostatin in inhibiting the release of growth hormone.

U.S. Pat. No. 4,280,953 discloses compounds of the formula

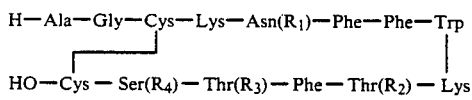

wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure provided that at least one R group is not hydrogen, and pharmaceutically acceptable nontoxic salts thereof. These compounds have an extended lifetime compared to somatostatin and act as inhibitors of pituitary growth hormone secretion, glucagon and insulin secretion of the pancreas, and secretion of vasoactive intestinal polypeptides, secretion, gastrin, and gastric acid.

Additionally, various scientific journal publications have disclosed additional somatostation analogues. For example, Veber et al., Nature 292, 55-58 (1981), discloses compounds of the formula

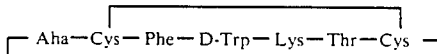

in which Aha is 7-aminoheptanoic acid and various fragments derived from this bicyclic structure. The bicyclic compounds were active in inhibiting growth hormone, glucagon, and insulin secretion.

However these compounds have been disclosed to be useful only for the specific purposes indicated, and there continues to be a need for active somatostatin analogues which protect blood vessel walls from lesions and activate phagocytes, two different uses of somatostatin.

SUMMARY OF THE INVENTION

Accordingly, it is an object of this invention to provide a method of stimulating phagocytosis in a vertebrate.

It is a further object of this invention to provide a method of stimulating phagocytosis in a vertebrate having a surplus of particles in the blood of said vertebrate.

It is yet another object of this invention to provide a method of protecting a vertebrate against bacterial and viral infections by increasing the clearing rate of particles by Kuppfer cells and macrophages.

It is a still further object of this invention to provide a method of removing immune complexes, therapeutic and diagnostic compositions, synthetic toxins, and endotoxins from the blood stream of a vertebrate.

It is another object of this invention to provide a method of preventing or treating blood vessel lesions caused by the presence of toxins.

It is still a further object of this invention to provide a method of preventing or treating biological membrane lesions and other types of membrane destabilizations in the liver of a human or mammal exposed to an endogenous or exogenous toxin.

These and other objects of the invention as will herinafter become more readily apparent, have been accomplished by providing a method of treating hepatic or blood vessel lesions by administering to a human or animal suspected of having one or more lesions an exogenous amount of a somatostatin analogue sufficient to reduce the number of severity of said lesions and by further providing a method of increasing phagocytosis in a vertebrate having a surplus of particles in the blood stream of said vertebrate, which comprises administering to said vertebrate an amount of a somatostatin analogue effective to increase the activity of phagocytes in said vertebrate in clearing said particles from said blood stream, wherein said analogue is selected from compounds of the formula

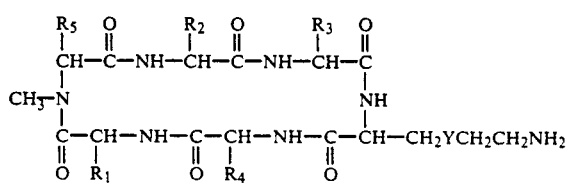

wherein

Y is $(CH_2)_m$ wherein m is 0, 1 or 2 or sulfur such that the sulfur may be in any position along the chain;

$R_1$ and $R_2$ are independently lower alkyl, benzyl, substituted benzyl where the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lower alkoxy, hydroxy, halogen amino or nitro;

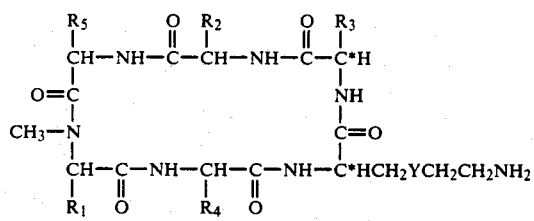

wherein

Y is $(CH_2)_m$ wherein m is 0, 1, or 2 or sulfur such that the sulfur may be in any position along the chain;

$R_1$ and $R_2$ are independently lower alkyl, benzyl, substituted benzyl wherein the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lowwer alkoxy, hydroxy, halogen amino or nitro; and the two asymmetric centers marked with an asterisk (*) may be either D or L, provided the two centers of asymmetry are the same, while the other asymmetric centers are D;

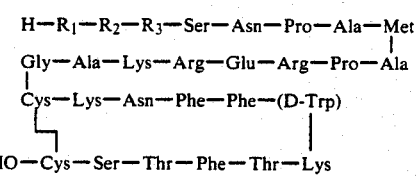

in which A represents an L-, D- or DL-5- or 6-fluoro-, bromo-, chloro-, or iodotryptophyl radical;

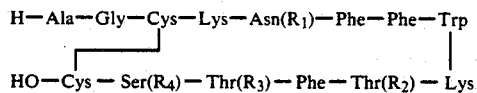

in which
  Bmp represents a desaminocysteine radical,
  X represents Asn or His,
  trp represents D-Trp that may be substituted in the phenyl ring by a halogen atom, and
  Y represents the radical of a secondary α-amino acid having a maximum of 8 carbon atoms;

```
    ┌─────────────────────────────────────┐
A'—Cys—B—Asn—Phe—Phe—trp—Lys(Ac)—
                                     │
         ┌───────────────────────────┘
         —Thr—Phe—Thr—Ser—cys—OH
``` in which
  A' represents H-Ala-Gly-, Ac-Ala-Gly-, H- or Ac-.
  B represents Lys, Lys(Ac) or Lys(X) (wherein X is an ε-amino protecting group).
  trp represents L-Trp, D-Trp or an analogous radical which carries in the indole nucleus a halogen atom,
  cys represents L-Cys or D-Cys and
  Ac represents an acyl radical of an optionally substituted alkanecarboxylic acid present at the free amino group;

```
    ┌────────────────────────────────────┐
    Asn—Phe—Phe—trp—Lys—Thr—Phe—Gaba(Ar)
``` in which
  trp represents L-Trp or D-trp in which the phenyl ring may be substituted with a halogen atom, and
  Gaba(Ar) represents the residue of a γ-aminobutyric acid substituted with a cyclic hydrocarbyl radical;

```
H—R1—R2—R3—Ser—Asn—Pro—Ala—Met
                                │
Gly—Ala—Lys—Arg—Glu—Arg—Pro—Ala
 │
Cys—Lys—Asn—Phe—Phe—(D-Trp)
 │                        │
HO—Cys—Ser—Thr—Phe—Thr—Lys
``` in which $R_1$ is Ser or des $R_1$, $R_2$ is Ala or des $R_2$, and $R_3$ is Asn or des $R_3$ and linear versions thereof in which the disulfide bridge is replaced by hydrogen sulfides;

```
H—Ala—Gly—Cys—Lys—Asn(R1)—Phe—Phe—Trp
           │                          │
HO—Cys—Ser(R4)—Thr(R3)—Phe—Thr(R2)—Lys
``` wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure provided that at least one R group is not hydrogen, and pharmaceutically acceptable nontoxic salts thereof; or cyclo[phe-Phe-trp-Lys-Thr-Phe] in which phe represents D-, L-, or DL-phenylalanine and trp represents D-, L-, or DL-tryptophan.

DESCRIPTION OF THE PREFERRED EMBODIMENTS

The structure of somatostatin has been established by analytical investigations and chemical synthesis. Somatostatin is a cyclic tetradecapeptide having the following structure:

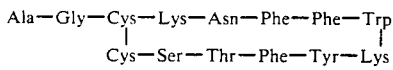

Somatostatin can be isolated from bovine hypothalamic extracts, as disclosed in Brazeau et al, *Science*, 179, 77 (1973) or can be synthesized, for example, as disclosed in Rivier et al, *Compt. Rend., Ser. D*, 276, 2737 (1973); Sarantakis et al, *Biochem. Biophys. Res. Commun.*, 54, 234 (1973); Yamashiro et al, ibid, 882; and Coy et al, ibid, 1267, all of which disclosures of isolation and syntheses being hereby incorporated by reference. The synthetic linear form of the peptide shows identical biological activity to the natural cyclic or synthetic cyclic (oxidized) forms, all of which are considered to be encompassed by the single term "somatostatin" for the purposes of this invention. All of the somatosatin analogues of the invention can be synthesized by the specific methods discussed later or by the general methods of peptide synthesis discussed in the above-incorporated references, with substitutions of amino acids as necessary, as is well known to those skilled in the art of peptide synthesis.

Various previous studies have shown that somatostatin is effective for preventing deterioration of various animal tissues, such as the articles discussed in the prior art section of this application. The prior patent of two of the present inventors, U.S. Pat. No. 4,366,148, discloses that somatostatin is effective for preventing lesions of blood vessels, especially lesions of hepatic blood vessels in mammals. Applicants have now discovered that various analogues of somatostatin are more active than was somatostatin itself for this purpose and are also more effective in increasing the activity of phagocytes in vertebrates than is somatostatin. The use of somatostatin itself in increasing the activity of phagocytes is described in an application by Szabo and Usadel which was filed on even date with this application. Thus, the present invention encompasses analogues of somatostatin having enhanced activity in promoting the activity of phagocytes or protecting hepatic tissue against lesions. These applications of the somatostatin analogues will be discussed separately for the sake of convenience, with the phagocyte stimulating activity being discussed first.

Phagocyte activity can be stimulated by administering one of the somatostatin analogues set forth in the summary of the invention section to a vertebrate having a surplus of particles in the blood stream of said vertebrate in an amount effective to increase the rate of phagocytosis in said vertebrate. Thus, the somatostatin analogue leads to more rapid clearing of particles from the blood stream of vertebrates when administered in accordance with the present invention than would occur in the absence of the administered somatostatin analogue.

By "particles" is meant substances in the colloidal particle size range as commonly understood. Typical colloidal particles have an average diameter in the range from 10 to 300 μm. However, since phagocytes recognize and avoid naturally occurring particles present in the blood stream, such as red blood cells, such materials will not be removed when phagocytosis is stimulated in accordance with this invention. Thus, as used herein, "particle" does not encompass blood cells or other natural molecules, complexes, or cells that are present in amounts normally found in the vertebrate and which are not normally engulfed by phagocytes. However, immune complexes, such as would be present either in an infection (e.g., by bacteria) or an autoimmune disease, are considered to be within the scope of the term "particles". The same is true of damaged or modified cells or other substances which are normally removed by phagocytes.

The present invention is intended principally to aid in the clearing of viruses, bacteria, and immune complexes from the blood stream of vertebrates. However, the invention may also be carried out on a vertebrate which was previously injected with a diagnostic or therapeutic agent in order to reduce the amount of agent present in the blood stream. For example, liposomes are often used as carriers of therapeutic agents and would be removed by the stimulated phagocytosis of the present invention. Other examples of colloidal particles against which the present invention can be used include endotoxins and synthetic toxins.

The somatostatin analogues that can be used in the practice of this invention are those having a formula selected from the group consisting of

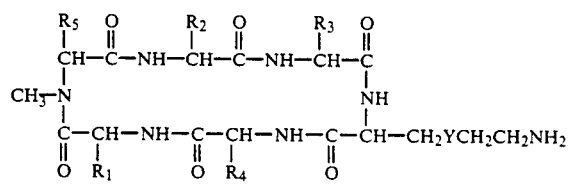

wherein

Y is $(CH_2)_m$ wherein m is 0, 1 or 2 or sulfur such that the sulfur may be in any position along the chain;

$R_1$ and $R_2$ are independently lower alkyl, benzyl, substituted benzyl where the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lower alkoxy, hydroxy, halogen amino or nitro;

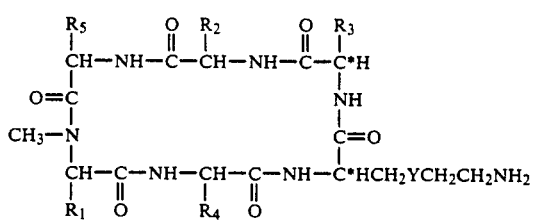

wherein

Y is $(CH_2)_m$ wherein m is 0, 1, or 2 or sulfur such that the sulfur may be in any position along the chain;

$R_1$ and $R_2$ are independently lower alkyl, benzyl, substituted benzyl where the substituent may be one or two of lower alkyl, halogen, hydroxy, amino, nitro or lower alkoxy; and lower alkyl substituted with a 5- or 6-membered heterocyclic ring;

$R_3$ is 3-indolylmethyl or substituted 3-indolylmethyl wherein the substituent may be lower alkyl, lower alkoxy, or halogen;

$R_4$ is lower alkyl, hydroxy lower alkyl, benzyl, carboxy lower alkyl, amino lower alkyl or substituted benzyl wherein the substituent may be lower alkyl; lower alkoxy, hydroxy, halogen, amino or nitro, and $R_5$ is hydrogen, lower alkyl, benzyl, or substituted benzyl wherein the substituent is lower alkyl, lower alkoxy, hydroxy, halogen amino or nitro; and the two asymmetric centers marked with an asterisk (*) may be either D or L, provided the two centers of asymmetry are the same, while the other asymmetric centers are D;

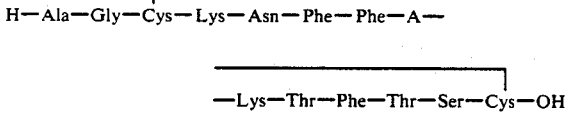

in which A represents an L-, D- or DL-5- or 6-fluoro-, homo-, chloro-, or iodotryptophenyl;

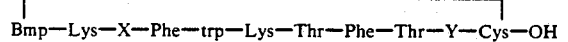

in which

Bmp represents a desaminocysteine radical,

X represents Asn or His, trp represents D-Trp that may be substituted in the phenyl ring by a halogen atom, and Y represents the radical of a secondary α-amino acid having a maximum of 8 carbon atoms;

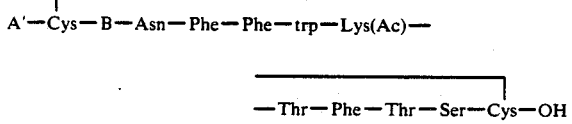

in which

A' represents H-Ala-Gly-, Ac-Ala-Gly-, H- or Ac-.

B represents Lys, Lys(Ac) or Lys(X) (wherein X is an ε-amino-protecting group), trp represents L-Trp, D-Trp or an analogous radical which carries in the indole nucleus a halogen atom, cys represents L-Cys or D-Cys and Ac represents an acyl radical of an optionally substituted alkanecarboxylic acid present at the free amino group;

in which trp represents L-Trp or D-Trp in which the phenyl ring may be substituted with a halogen atom, and Gaba(Ar) represents the residue of a γ-aminobutyric acid substituted with a cyclic hydrocarbyl radical;

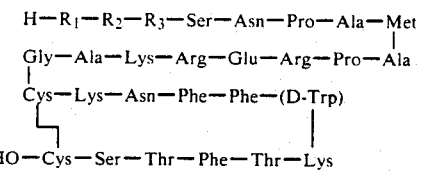

in which $R_1$ is Ser or des $R_1$, $R_2$ is Ala or des $R_2$, and $R_3$ is Asn or des $R_3$ and linear versions thereof in which the disulfide bridge is replaced by hydrogen sulfides;

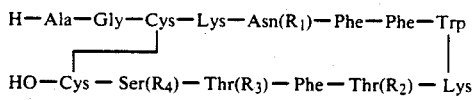

wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure provided that at least one R group is not hydrogen, and pharmaceutically acceptable nontoxic salts thereof; and cyclo[phe-Phe-trp-Lys-Thr-phe] in which phe represents D-, L-, or DL-phenylalanine and trp represents D-, L-, or DL-tryptophane.

Somatostatin analogues may be used to treat any vertebrate having functioning phagocytes in its blood stream or organs (especially any mammal), although treatment of humans is preferred. Suitable dosages of somatostatin analogues are 0.1 μg to 10 mg/kg of body weight, preferably 0.02 to 0.50 mg/kg, and more preferably 0.06 to 0.20 mg/kg. Administration may be in a single dose or may be spread out over time by administration of multiple small doses or by slow continuous intravenous administration of a dilute solution of the somatostatin analogue. The maximum dose per day should not exceed 10 mg/kg of body weight. Since the somatostatin analogues have similar molecular weights (generally in the range of 700–800), it is not necessary to calculate dosages on a mmole/kg basis. However, for a compound having a molecular weight of 750, 0.02 to 50 mg/kg would correspond to 0.027 to 0.67 μmole/kg. These molar amounts can be used as the preferred range should any question arise.

The dosage may be administered by intravenous, subcutaneous or intramuscular injection or intragastrically. Inhalation or rectal administration is also suitable. Administration by intravenous or subcutaneous injection is preferred. When administered in the form of an injection, any non-toxic pharmaceutical carriers may be used, provided that the carrier does not cause hydrolysis of the somatostain analogue's peptide bonds or otherwise interfere with activity. Suitable carriers include water, aqueous solutions of non-toxic salts and organic compounds, and non-toxic organic solvents, such as ethanol. Preferred are isotonic aqueous solutions, such as solution of NaCl and glucose. Most preferred for subcutaneous injections are solutions containing protamine sulfate and $ZnCl_2$ (about 0.05% and about 0.13 mg/ml, respectively) as these materials prolong the activity of somatostain, particularly when injected subcutaneously.

A somatostatin analogue may be administered alone or concurrently with other medicinal materials. Preferred is administration with other materials that also alleviate the condition being treated, for example, antibiotics or immune response stimulants, such as interferon, when an infection is being countered.

Administration may occur after the presence of an infection is suspected or confirmed, or under conditions in which surplus particles would be expected to be present, for example, after administration of radioactive liposomes in a diagnostic technique.

The effectiveness of somatostatin analogues in increasing phagocytosis has been demonstrated in a model study using carbon particles. Rats were injected either with saline or with a colloidal carbon suspension, and the time required for clearing of colloidal particles from the blood stream was measured. In a comparative experiment, zymosan, an agent known to increase the activity or phagocytes, was administered instead of the somatostatin analogue. In rats which received injections of saline, the disappearance of colloidal carbon from the blood was virtually linear, an expected result based on previous studies by others. Administration of a somatostatin analogue markedly accelerated the carbon clearance, even more so than for somatostatin itself. Phagocytosis of carbon particles was particularly enhanced for Kuppfer cells, the fixed histiocytes present on the walls of the liver sinusoids, and other macrophages in the liver, lung and spleen. Some somatostatin analogues were demonstrated by these studies to be more effective than zymosan in stimulating clearing potency.

In the second aspect of the present invention, somatostatin analogues have been shown in the present studies to be effective agents for preventing lesions of blood vessels, especially lesions of hepatic blood vessels in mammals. In addition somatostatin analogues have been shown to be effective in preventing deterioration of biological membranes in the livers of mammals. By deterioration is meant a lesion or any state of membrane health that intervenes between a state of proper membrane health and a lesion. States that would lead to the formation of a lesion if untreated are known as prelesions. By lesion is meant any pathological discontinuity of tissue or loss of function of a membrane or vascular wall. Somatostatin analogues are also expected to be effective in the treatment of pre-existing lesions and membrane deterioration. Somatostatin analogues are believed to stabilize biological membrane against the formation of new lesions or deterioration and to reduce the extent of existing lesions and membrane deterioration.

The present invention comprises administering a somatostatin analogue to prevent and treat hepatic and vascular lesions caused by a variety of exogenous and endogenous toxins (known collectively as chemical toxins) and other agents; in fact, for any agent which causes deterioration of cellular membranes, particularly hepatic vessels and membranes. Examples of agents that cause vascular damage and against which somatostatin analogues are expected to be effective include endogenous agents, such as vasoactive amines, and exogenous agents, such as therapeutic and diagnostic drugs like sulfa drugs, penicillin derivatives, estrogens, and chemotherapeutic agents as well as plant and animal toxins. Vascular deterioration as a result of disease, for example endotoxic shock, Gram-negative bacterial sepsis, and disseminated intravascular coagulation, should also be amenable to treatment or prevention by somatostatin analogues.

The structure of somatostatin analogues useful in the practice of this invention have been disclosed above in the discussion relating to stimulation of phagocytes.

A somatostatin analogue can be used to treat any vertebrate, although treatment of mammals, especially humans is preferred. Suitable dosages of somatostatin analogues are 10 μg to 10 mg/kg of body weight. Preferred are dosages in the range of 0.1 to 1.5 mg/kg. Most preferred is about 1.25 mg/kg. Molar amounts may be calculated as shown in the previous section if desired. Administration may be in a single dose or may be spread out over time by administration of multiple small doses or by slow intravenous administration of a dilute solution of the somatostatin analogue. The maximum dose per day should not exceed 10 mg/kg of body weight.

Administration techniques suitable for this aspect of the invention are identical with those described for the method of increasing phagocyte activity.

A somatostatin analogue may be administered alone or concurrently with other medical materials. Preferred is administration with other materials that also alleviate the action of lesion-causing agents, such as prostaglandins.

Administration may occur after the presence of a lesion is suspected or confirmed, or under conditions in which lesions might be expected to occur, for example, during chemotherapy.

The effectiveness of somatostatin has been demonstrated in a model study using the toxin phalloidin, a toxin isolated from the poisonous mushroom *Amanita phalloides*. This toxin kills rats within about 4 hours after intraperitoneal injection. Rats injected with 0.12 mg phalloidin per 100 g body weight (i.p.) show a massive increase in liver size accompanied by hemorrhage. In a control group of rats given phalloidin but no somatostatin analogue, 22 of 24 rats died within 2-4 hours. Autopsy of these rats revealed a 70% average increase in liver weight, and light microscopy showed vacuolization of hepatocytes, congestion, and hemorrhagic necrosis. A significantly smaller number of rats in the test group of animals that were treated with both phalloidin and somatostatin died. Histologic examination revealed milder vacuolization of hepatocytes and less congestion—even that that which occurred when somatostatin itself was used.

These results were confirmed in additional biochemical and morphologic experiments. In both cases, rats were given saline (control), phalloidin alone, or phalloidin and a somatostatin analogue. Somatostatin analogues were given in subcutaneous injections in a solution of protamine sulfate and zinc chloride in order to prolong its effectiveness, or in normal saline.

In the biochemical experiments, the animals were also injected with Evans blue 15 min before autopsy. At autopsy the portal vein was perfused in situ with 20 ml of saline to remove blood from hepatic vaculature. Phalloidin caused a time dependent increase in the hepatic uptake of Evans blue, indicative of leakage of blood into the tissue through blood vessel lesions. Somatostatin analogue treatment virtually abolished this enhanced uptake of the dye. In the morphologic experiments, groups of rats were also injected with colloidal carbon (India ink, 0.1 mg/100 g i.v.) 15 min before autopsy. At that time pieces of liver were processed for subsequent light or electron microscopic studies. Light microscopy revealed a uniform uptake of carbon particles in Kuppfer cells of the liver of control animals. In rats given phalloidin, carbon labeling of sinusoidal macrophages was decreased in the centrilobular areas, while early deposits of carbon were seen along the sinusoidal walls in the periportal regions. Subsequently, these areas showed severe congestion and hemorrhage. Somatostatin analogue pretreatment markedly decreased the differential distribution of India ink in the liver after phalloidin administration and virtually abolished the carbon labeling of sinusoidal walls.

The above disclosure generally describes the present invention. A more complete understanding can be obtained by reference to the following specific examples, which are provided herein for purposes of illustration only and are not intended to be limiting unless otherwise specified.

EXAMPLES

All of the experiments described below were performed in female Sprague-Dawley rats (ESS Laboratories, Lynnfield, Mass.) with an initial body weight of 150–180 g, and with unlimited access to Purina laboratory chow and tap water. Control and experimental groups consisted of 3–4 rats. Each experiment was repeated at least twice and the results were pooled. Analogue I is cyclo[L-Pro-Phe-D-Trp-Lys-Thr-L-Phe]. Analogue II is cyclo[L-Phe-Phe-L-Trp-Lys-Thr-D-Phe]. These are preferred compounds for all aspects of the invention. The compound can be synthesized according to the procedure described in Veber et al., Nature, 292, 55–58 (1981), which is herein incorporated by reference. Basically, the linear peptide is prepared by a solid phase technique, for example, using a Beckman 990 peptide synthesizer following the protocol described in Strachan et al, J. Med. Chem., 22, 586–588 (1979), which is herein incorporated by reference. The linear peptide can then be cyclized by the technique of Veber et al, Proc. Natl. Acad. Sci. USA, 75, 2636–2640 (1978), which is also herein incorporated by reference. Linear or cyclic somatostatin (Serono) or a somatostatin analogue was injected under mild ether anesthesia at 50 $\mu$g in 0.5 ml of saline into the jugular vein once daily for 3 consecutive days prior to injection with carbon. Control animals were injected with the same amount of saline. In all of the carbon clearance experiments, 0.1 ml/100 g of the supernatant of centrifuged (3000 rpm/15 min) colloidal carbon (Wagner's india ink) was injected i.v. under mild ether anesthesia. Blood samples (50 $\mu$l) were obtained with heparinized glass capillaries and by puncture of the retro-orbital venous plexus at 3, 6, 12 and 24 minutes after the administration of carbon. The blood samples were lysed in 2 ml of 0.1% $Na_2CO_3$ solution and the quantity of carbon in the blood was measured. The results are shown in Table 1.

TABLE 1

| Treatment | India ink ($\mu$l/ml blood) | | | |
|---|---|---|---|---|
| | 3 min | 6 min | 12 min | 24 min |
| Saline | 17.7 ± 3.1 | 13.7 ± 2.6 | 9.7 ± 1.8 | 5.7 ± 1.1 |
| Regular linear somatostatin | 11.7 ± 0.1 | 11.9 ± 2.6 | 5.3 ± 1.4 | 2.6 ± 0.1 |
| Analogue I | 12.5 ± 3.0 | 6.9 ± 0.9 | 2.6 ± 0.7 | 2.4 ± 0.5 |
| Analogue II | 13.2 ± 2.0 | 5.6 ± 0.5 | 3.2 ± 0.9 | 1.8 ± 0.2 |

In rats which received daily injections of saline (0.5 ml), i.v., the disappearance of colloidal carbon from the blood was virtually linear and identical to absolute control rats in other experiments (not shown). Administration of somatostatin analogues markedly accelerated the carbon clearance; this effect was most dramatic during the first 6–12 minutes. However, Analogues I and II were both more potent than somatostatin (i.e., they produced lower levels of carbon at the late time intervals) and faster acting (i.e., they produced greater carbon clearance at 6 minutes than did somatostatin).

The liver protection studies included the effect of somatostatin and analogues on liver injury induced by galactosamine or phalloidin. Galactosamine-induced hepatic necrosis and inflammation was produced by injecting rats with 1 g/kg of galactosamine i.p. at 0 hr. Regular somatostatin was injected at 250 $\mu$g, analogues at 125 $\mu$g i.p. at −30 and 30 120 min. The animals were killed at 28 hr after galactosamine. Liver damage was measured by the elevation of serum transaminase (SGOT) and by liver histology (scale: 0–4 with 4 indicating the greatest damage). The results are shown in Table 2.

TABLE 2

| Treatment | SGOT (U/l) | Liver histology (Scale:0–4) |
|---|---|---|
| Galactosamine | 1417 ± 416 | 2.7 ± 0.3 |
| Galactosamine + somatostatin | 1757 ± 681 | 2.6 ± 0.3 |
| Galactosamine + Analogue I | 573 ± 138 | 1.1 ± 0.1 |
| Galactosamine + Analogue II | 700 | 1.0 |

Again, the analogues are more potent than regular somatostatin.

The invention now being fully described, it will be apparent to one of ordinary skill in the art that many changes and modifications can be made thereto without departing from the spirit or scope of the invention as set forth herein.

What is claimed as new and desired to be claimed by Letters Patent of the United States is:

1. A method of increasing clearance of exogenous colloidal particles from blood, which comprises:
   administering by inhalation, intravenous injection, subcutaneous injection, intramuscular injection, intragastrically or rectally to a vertebrate having a surplus of particles in the blood stream of said vertebrate an amount sufficient to increase the activity of phagocytes in said vertebrate of a somatostatin analogue of the formula

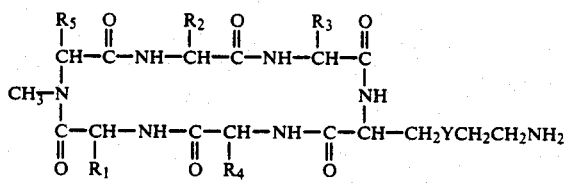

wherein

Y is $(CH_2)_m$ wherein m is 0, 1 or 2 or sulfur such that the sulfur is in any position along the chain;

$R_1$ and $R_2$ are independently lower alkyl; benzyl; substituted benzyl where the substituent is one or two of lower alkyl, halogen, hydroxy, amino, nitro or lower alkoxy; or lower alkyl substituted with a 5- or 6-membered heterocyclic ring;

$R_3$ is 3-indolylmethyl or substituted 3-indolylmethyl wherein the substituent is lower alkyl, lower alkoxy, or halogen;

$R_4$ is lower alkyl, hydroxy lower alkyl, benzyl, carboxy lower alkyl, amino lower alkyl or substituted benzyl wherein the substituent is lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro;

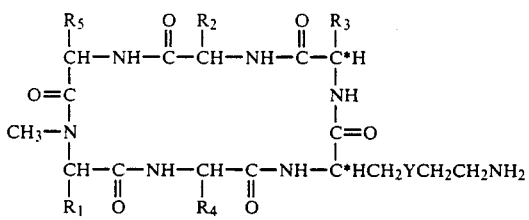

wherein

Y is $(CH_2)_m$ wherein m is 0, 1, or 2 or sulfur such that the sulfur is in any position along the chain;

$R_1$ and $R_2$ are independently lower alkyl; benzyl; substituted benzyl where the substituent is one or two of lower alkyl, halogen, hydroxy, amino, nitro or lower alkoxy; or lower alkyl substituted with a 5- or 6-membered heterocyclic ring;

$R_3$ is 3-indolylmethyl or substituted 3-indolylmethyl wherein the substituent is lower alkyl, lower alkoxy, or halogen;

$R_4$ is lower alkyl, hydroxy lower alkyl, benzyl, carboxy lower alkyl, amino lower alkyl or substituted benzyl wherein the substituent is lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro; and the two asymmetric centers marked with an asterisk are either D or L, provided the two centers of asymmetry are the same, while the other asymmetric centers are D;

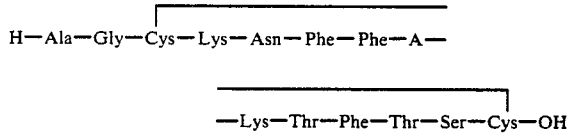

in which A represents an L-, D- or DL-5- or 6-fluoro-, bromo-, chloro-, or iodotryptophyl radical;

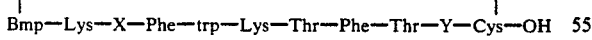

in which

Bmp represents a desaminocysteine radical,

X represents Asn or His, trp represents D-Trp or D-Trp that is substituted in the phenyl ring by a halogen atom, and Y represents the radical of a secondary α-amino acid having a maximum of 8 carbon atoms;

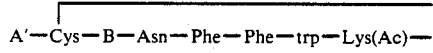

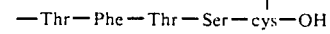

in which

A' represents H-Ala-Gly-, Ac-Ala-Gly-, H- or Ac-;

B represents Lys, Lys(Ac) or Lys(X) wherein X is an ε-amino-protecting group;

trp represents L-Trp, D-Trp or an analogous radical which carries in the indole nucleus a halogen atom;

cys represents L-Cys or D-Cys and

Ac represents an acyl radical of a substituted or unsubstituted alkanecarboxyclic acid present at the free amino group;

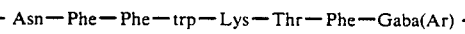

in which trp represents unsubstituted L-Trp or D-Trp or an L-Trp or D-Trp in which the phenyl ring is substituted with a halogen atom, and Gaba(Ar) represents the residue of a γ-aminobutyric acid substituted with a cyclic hydrocarbyl radical;

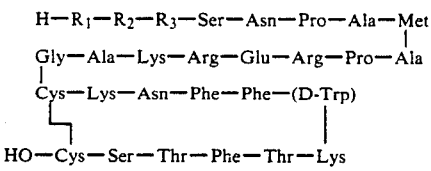

in which $R_1$ is Ser or des $R_1$, $R_2$ is Ala or des $R_2$, and $R_3$ is Asn or des $R_3$ and linear versions thereof in which the disulfide bridge is replaced by hydrogen sulfides;

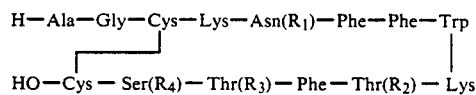

wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure, provided that at least one R group is not hydrogen, and pharmaceutically acceptable nontoxic salts thereof;

or cyclo [phe-Phe-trp-Lys-Thr-phe] in which phe represents D-, L-, or DL-Phenylalanine and trp represents D-, L-, or DL-tryptophan.

2. The method of claim 1, wherein said particles are bacteria or viruses.

3. The method of claim 1, wherein said particles are immune complexes.

4. The method of claim 1, wherein said particles are therapeutic or diagnostic agents.

5. The method of claim 1, wherein said particles are endotoxin.

6. The method of claim 1, wherein said somatostatin analogue is administered in an amount of from 0.02 to 1.5 mg/kg of body weight.

7. The method of claim 6, wherein said amount is from about 0.06 to about 1.0 mg/kg of body weight.

8. The method of claim 1, wherein said administering is by intravenous or subcutaneous injection.

9. The method of claim 1, wherein said administering is to a human.

10. A method of treating vascular lesions, comprising: administering by inhalation, intravenous injection, subcutaneous injection, intramuscular injection, intragastrically or rectally to a human or mammal suspected of having one or more vascular lesions an amount sufficent to reduce the number or severity of said lesions of a somatostatin analogue of the formula

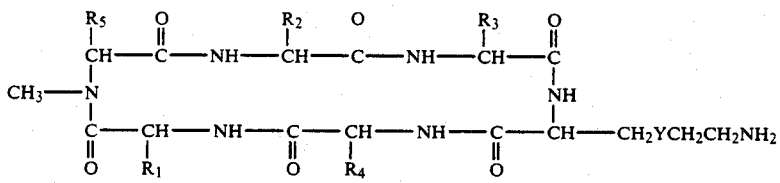

wherein

Y is $(CH_2)_m$ wherein m is 0, 1 or 2 or sulfur such that the sulfur is in any position along the chain;

$R_1$ and $R_2$ are independently lower alkyl; benzyl; substituted benzyl where the substituent is one or two of lower alkyl, halogen, hydroxy, amino, nitro or lower alkoxy; or lower alkyl substituted with a 5- or 6-membered heterocyclic ring;

$R_3$ is 3-indolylmethyl or substituted 3-indolylmethyl wherein the substituent is lower alkyl, lower alkoxy, or halogen;

$R_4$ is lower alkyl, hydroxy lower alkyl, benzyl, carboxy lower alkyl, amino lower alkyl or substituted benzyl wherein the substituent is lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro;

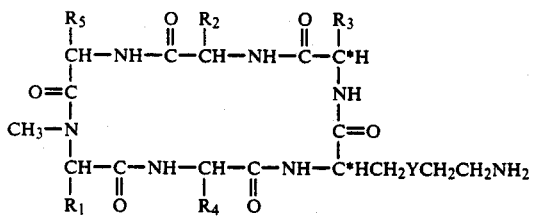

wherein

Y is $(CH_2)_m$ wherein m is 0, 1, or 2 or sulfur such that the sulfur is in any position along the chain;

$R_1$ and $R_2$ are independently lower alkyl; benzyl; substituted benzyl where the substituent is one or two of lower alkyl, halogen, hydroxy, amino, nitro or lower alkoxy; or lower alkyl substituted with a 5- or 6-membered heterocyclic ring;

$R_3$ is 3-indolylmethyl or substituted 3-indolylmethyl wherein the substituent is lower alkyl, lower alkoxy, or halogen;

$R_4$ is lower alkyl, hydroxy lower alkyl, benzyl, carboxy lower alkyl, amino lower alkyl or substituted benzyl wherein the substituent is lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen amino or nitro; and the two asymmetric centers marked with an asterisk are either D or L, provided the two centers of asymmetry are the same, while the other asymmetric centers are D;

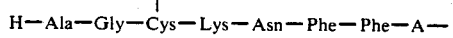
H—Ala—Gly—Cys—Lys—Asn—Phe—Phe—A—

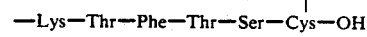
—Lys—Thr—Phe—Thr—Ser—Cys—OH in which A represents an L-, D- or DL-5- or 6-fluoro-, bromo-, chloro-, or iodotryptophyl radical;

Bmp—Lys—X—Phe—trp—Lys—Thr—Phe—Thr—Y—Cys—OH in which

Bmp represents a desaminocysteine radical,

X represents Asn or His, trp represents D-Trp or D-Trp that is substituted in the phenyl ring by a halogen atom, and Y represents the radical of a secondary α-amino acid having a maximum of 8 carbon atoms;

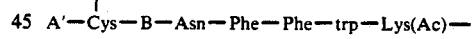
A'—Cys—B—Asn—Phe—Phe—trp—Lys(Ac)—

—Thr—Phe—Thr—Ser—cys—OH in which

A' represents H-Ala-Gly-, Ac-Ala-Gly-, H- or Ac-;

B represents Lys, Lys(Ac) or Lys(X) wherein X is an ε-amino-protecting group, trp represents L-Trp, D-Trp or an analogous radical which carries in the indole nucleus a halogen atom, cys represents L-Cys or D-Cys and Ac represents an acyl radical of a substituted or unsubstituted alkanecarboxylic acid present at the free amino group;

—Asn—Phe—Phe—trp—Lys—Thr—Phe—Gaba(Ar)— in which trp represents unsubstituted L-Trp or D-Trp or an L-Trp or D-Trp in which the phenyl ring is substituted with a halogen atom; and Gaba(Ar) represents the residue of a γ-aminobutyric acid substituted with a cyclic hydrocarbyl radical;

```
H—R₁—R₂—R₃—Ser—Asn—Pro—Ala—Met
                                |
Gly—Ala—Lys—Arg—Glu—Arg—Pro—Ala
 |
Cys—Lys—Asn—Phe—Phe—(D-Trp)
 └─┐                   |
HO—Cys—Ser—Thr—Phe—Thr—Lys
``` in which $R_1$ is Ser or des $R_1$, $R_2$ is Ala or des $R_2$, and $R_3$ is Asn or des $R_3$ and linear versions thereof in which the disulfide bridge is replaced by hydrogen sulfides;

```
H—Ala—Gly—Cys—Lys—Asn(R₁)—Phe—Phe—Trp
          └─┐                       |
HO—Cys — Ser(R₄)— Thr(R₃)— Phe — Thr(R₂) — Lys
``` wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure, provided that at least one R group is not hydrogen, and pharmaceutically acceptable nontoxic salts thereof; or cyclo[phe-Phe-trp-Lys-Thr-phe] in which phe represents D-, L-, or DL-phenylalanine and trp represents D-, L-, or DL-tryptophan.

11. The method of claim 10, wherein said lesions are caused by a chemical toxin.

12. The method of claim 10, wherein said somatostatin analogue is administered in an amount of from 0.1 to 1.5 mg/kg of body weight.

13. The method of claim 12, wherein said amount is about 1.25 mg/kg of body weight.

14. The method of claim 10, wherein said administering is by intravenous or subcutaneous injection.

15. The method of claim 10, wherein somatostatin analogue is administered to a human.

16. A method of stabilizing biological membranes in vivo, comprising:
administering by inhalation, intravenous injection, subcutaneous injection, intramuscular injection, intragastrically or rectally to a human or other mammal suspected of having deterioration of a biological membrane in the liver of said human or mammal an amount of a somatostatin analogue having a formula of claim 10 sufficient to prevent further deterioration or reduce the extent of deterioration of said membrane.

17. The method of claim 16, wherein said deterioration is caused by a chemical toxin.

18. The method of claim 16, wherein said destabilization is a lesion.

19. The method of claim 16, wherein said somatostatin analogue is administered in an amount of from 0.1 to 1.5 mg/kg of body weight.

20. The method of claim 16, wherein said administering is by intravenous or subcutaneous injection.

21. The method of claim 16, wherein said administering is to a human.

* * * * *